(12) United States Patent
Olson et al.

(10) Patent No.: US 7,767,875 B2
(45) Date of Patent: Aug. 3, 2010

(54) WETNESS INDICATOR FOR ALERTING A WEARER TO URINATION

(75) Inventors: Christopher P. Olson, Neenah, WI (US); Larry H. Sawyer, Neenah, WI (US); Shirlee A. Weber, Neenah, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 1750 days.

(21) Appl. No.: 10/038,863

(22) Filed: Dec. 31, 2001

(65) Prior Publication Data

US 2003/0125682 A1 Jul. 3, 2003

(51) Int. Cl.
*A61F 13/15* (2006.01)
*A61F 13/20* (2006.01)

(52) U.S. Cl. .................. 604/361; 604/367

(58) Field of Classification Search ............. 604/361, 604/367, 374, 378–379, 381, 385, 385.01, 604/364
See application file for complete search history.

(56) References Cited

U.S. PATENT DOCUMENTS

| | | | |
|---|---|---|---|
| 3,849,241 A | 11/1974 | Butin et al. | |
| 3,918,454 A * | 11/1975 | Korodi et al. | 604/361 |
| 4,663,220 A | 5/1987 | Wisneski et al. | |
| 4,673,403 A * | 6/1987 | Lassen et al. | 604/385.17 |
| 4,704,116 A | 11/1987 | Enloe | |
| 4,761,258 A | 8/1988 | Enloe | |
| 4,940,464 A | 7/1990 | Van Gompel et al. | |
| 4,960,477 A * | 10/1990 | Mesek | 156/209 |
| 5,046,272 A | 9/1991 | Vogt et al. | |
| 5,104,116 A | 4/1992 | Pohjola | |
| 5,147,343 A | 9/1992 | Kellenberger | |
| 5,224,405 A | 7/1993 | Pohjola | |
| 5,226,992 A | 7/1993 | Morman | |
| 5,425,725 A * | 6/1995 | Tanzer et al. | 604/368 |
| 5,494,622 A | 2/1996 | Heath et al. | |
| 5,575,785 A | 11/1996 | Gryskiewicz et al. | |
| 5,601,542 A | 2/1997 | Melius et al. | |
| 5,649,914 A | 7/1997 | Glaug et al. | |
| 5,658,268 A | 8/1997 | Johns et al. | |

(Continued)

FOREIGN PATENT DOCUMENTS

DE 36 08 114 A1 9/1987

(Continued)

OTHER PUBLICATIONS

PCT International Search Report dated Apr. 24, 2003.

*Primary Examiner*—Michele Kidwell
(74) *Attorney, Agent, or Firm*—Armstrong Teasdale, LLP

(57) ABSTRACT

A toilet training wetness indicator for alerting a wearer to urination and a garment incorporating such an element. The toilet training wetness indicator, which may be an insertable wetness indicator or integrated directly into a garment, such as training pants, comprises a liquid permeable enclosure having a liquid absorbent body enclosed therein. The liquid absorbent body absorbs liquid within the pants and applies hydraulic pressure to the enclosure upon absorption of a preselected amount of liquid. The enclosure limits expansion of the absorbent body so that the wetness indicator stiffens as liquid is absorbed. The wetness indicator has a first stiffness and is relatively pliable when dry and a second stiffness greater than the first stiffness upon absorption of the preselected amount of liquid.

28 Claims, 5 Drawing Sheets

U.S. PATENT DOCUMENTS

| | | | |
|---|---|---|---|
| 5,681,289 A | 10/1997 | Wilcox et al. | |
| 5,681,298 A | 10/1997 | Brunner et al. | |
| 5,702,376 A | 12/1997 | Glaug et al. | |
| 5,702,377 A | 12/1997 | Collier, IV et al. | |
| 5,766,389 A | 6/1998 | Brandon et al. | |
| 5,769,835 A | 6/1998 | Fell et al. | |
| 5,797,892 A | 8/1998 | Glaug et al. | |
| 5,814,035 A | 9/1998 | Gryskiewicz et al. | |
| 5,863,288 A * | 1/1999 | Baker | 604/378 |
| 5,885,264 A | 3/1999 | Matsushita | |
| 5,913,851 A | 6/1999 | Gryskiewicz et al. | |
| 5,921,974 A | 7/1999 | Kikuchi | |
| 5,935,118 A | 8/1999 | Gryskiewicz et al. | |
| 5,994,614 A * | 11/1999 | Wada et al. | 604/378 |
| 6,126,648 A | 10/2000 | Keck et al. | |
| 6,159,591 A | 12/2000 | Beihoffer et al. | |
| 6,162,961 A | 12/2000 | Tanner et al. | |
| 6,180,847 B1 | 1/2001 | Ahr et al. | |
| 6,221,460 B1 * | 4/2001 | Weber et al. | 428/131 |
| 6,245,410 B1 | 6/2001 | Hähnle et al. | |
| 6,330,735 B1 | 12/2001 | Hahn et al. | |
| 6,642,427 B2 | 11/2003 | Roe et al. | |
| 2003/0023214 A1 * | 1/2003 | DiSalvo et al. | 604/364 |

FOREIGN PATENT DOCUMENTS

| | | |
|---|---|---|
| EP | 0 217 032 A2 | 4/1987 |
| WO | WO 00/37009 | 6/2000 |
| WO | WO 01/88245 A2 | 11/2001 |
| WO | WO 02/091968 A2 | 11/2002 |
| WO | WO 03/051258 A1 | 6/2003 |

\* cited by examiner

WETNESS INDICATOR FOR ALERTING A WEARER TO URINATION

BACKGROUND OF THE INVENTION

The present invention relates generally to absorbent articles, and more particularly to a wetness indicator for use in absorbent articles to alert a wearer to urination.

Disposable absorbent articles such as diapers, training pants, other child care products, other infant care products and adult care products are highly absorbent and efficiently pull moisture away from the wearer, reducing skin irritation caused by prolonged wetness exposure. However, because these articles are so absorbent, wearers may not realize they have urinated, particularly if they are inexperienced toddlers who may not recognize the meaning of body sensations associated with urination. Thus, the wearer may not recognize their urination control failure or be aware the article should be changed. Many parents believe that children must be given a signal such as feeling uncomfortable and wet to facilitate toilet training by making the child more aware that the act of urination has occurred. However, some parents worry about the possibility of skin irritations and rashes caused by prolonged wetness against the skin if the articles are less absorbent to allow the child to sense wetness.

Some prior absorbent articles intended for toilet training include means for alerting a child that urination has occurred without leaving a substantial amount of wetness against the skin. One such prior absorbent article includes a temperature changing element which allows the wearer to feel a change in temperature, alerting them after urination has occurred. Another example includes an element which changes size after urination, expanding directly toward the wearer's crotch region. Still another example has high initial surface moisture immediately following urination but pulls moisture away from the wearer shortly thereafter.

Although there has been progress in articles for alerting a wearer to urination, there continues to be a need for articles such as toilet training aids which alert wearers to urination without allowing the skin to become wet.

SUMMARY OF THE INVENTION

Generally, a wetness indicator of the present invention for alerting a wearer to urination comprises a liquid permeable enclosure having a liquid absorbent body therein. The absorbent body absorbs liquid in the presence thereof and applies hydraulic pressure to the enclosure upon absorption of a preselected amount of liquid. The enclosure limits expansion of the absorbent body, stiffening the wetness indicator as liquid is absorbed. The wetness indicator has a first stiffness when dry and a second stiffness greater than the first stiffness upon absorption of the preselected amount of liquid.

The invention is further directed to a garment having an inner surface facing a wearer when wearing the garment and a wetness indicator generally as set forth above positioned relative to the inner surface for alerting the wearer when the inner surface becomes wet with liquid.

Other features of the present invention will be in part apparent and in part pointed out hereinafter.

BRIEF DESCRIPTION OF THE DRAWINGS

Corresponding reference characters indicate corresponding parts throughout the several views of the drawings.

Definitions

Within the context of this specification, each term or phrase below includes the following meaning or meanings:

"Attached to" refers to the joining, adhering, connecting, bonding, or the like, of two elements. Two elements will be considered to be attached to one another when they are attached directly to one another or indirectly to one another, such as when each is directly attached to intermediate elements.

"Bonded" refers to the joining, adhering, connecting, attaching, or the like, of two elements. Two elements will be considered to be bonded together when they are bonded directly to one another or indirectly to one another, such as when each is directly bonded to intermediate elements.

"Layer" when used in the singular can have the dual meaning of a single element or more than one element.

"Superabsorbent" refers to a water-swellable, water-insoluble organic or inorganic material capable, under the most favorable conditions, of absorbing at least about fifteen times its weight and, more desirably, at least about thirty times its weight in an aqueous solution containing 0.9 weight percent sodium chloride. The superabsorbent materials can be natural, synthetic and modified natural polymers and materials, or a combination of such materials. In addition, the superabsorbent materials can be inorganic materials, such as silica gels, or organic compounds such as cross-linked polymers.

Detailed Description of the Preferred Embodiments

Figure 1:
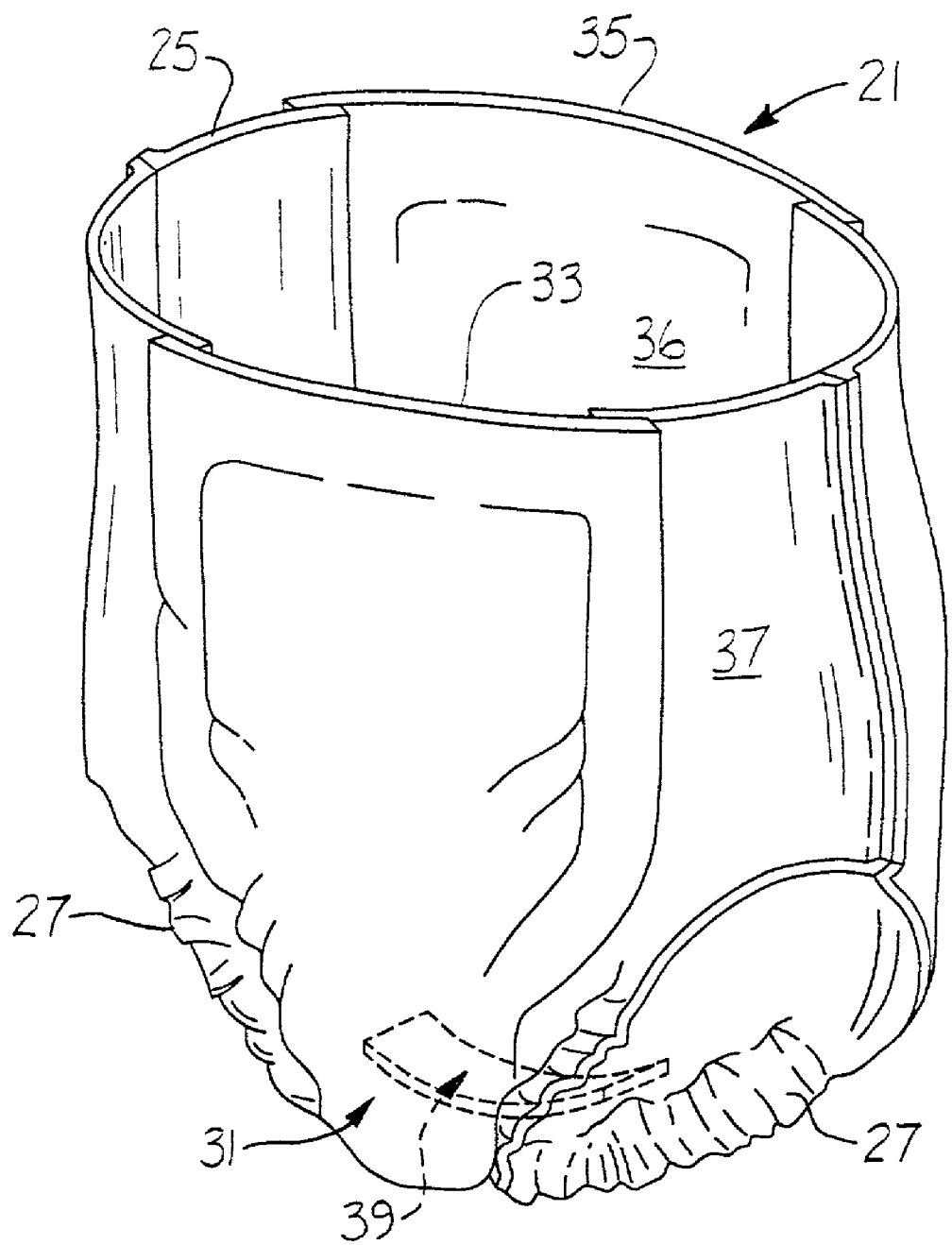
FIG. 1 is a perspective of training pants having a wetness indicator of the present invention therein.

Referring now to the drawings and more particularly to FIG. 1, a pair of toilet training pants, or more generally an absorbent article, is designated in its entirety by the reference numeral 21. The pants have a waist opening 25 and two leg openings 27. Where the pants 21 are worn, a crotch region, generally designated 31 and located generally between the leg openings 27, is generally positioned between the legs of the wearer. A front 33 of the training pants 21 extends generally upward from the crotch region 31, partially covering a lower abdomen of the wearer. A back 35 of the training pants 21 opposite the front 33 extends generally upward from the crotch region 31 to cover a buttocks of the wearer. The training pants 21 include an inner surface 36 facing the wearer and an outer surface 37 facing away from the wearer.

Various materials and methods for constructing training pants are disclosed in PCT Publication No. WO 00/37009 by Fletcher et al. published Jun. 29, 2000; U.S. Pat. No. 4,940,464 issued Jul. 10, 1990, to Van Gompel et al.; and U.S. Pat. No. 5,766,389 issued Jun. 16, 1998, to Brandon et al.; all of which are hereby incorporated by reference. An example of such training pants is marketed under the mark PULL-UPS® training pants by Kimberly-Clark Corporation of Neenah, Wis.

A wetness indicator for alerting a wearer to urination, generally designated by 39, is positioned generally between the leg openings 27 of the training pants 21. It should be understood that the wetness indicator 39 may be positioned elsewhere than in the crotch region 31 without departing from the scope of the present invention. It is envisioned that the position of wetness indicator 39 within the crotch region 31 may be different depending on whether the article is intended to be worn by girls or boys. As will be discussed in greater detail below, the wetness indicator 39 is configured to absorb liquid, such as urine. Therefore, placement in a more forward position of the crotch region 31 may be appropriate for boys, and placement in a more central position between the legs may be appropriate for girls. Before absorption of such liquid, the wetness indicator 39 is pliable and virtually imperceptible to the wearer, as will be discussed in greater detail below.

Although the wetness indicator 39 of the present invention is illustrated in FIG. 1 as being used in toilet training pants 21, the wetness indicator may also be used in conjunction with other garments and/or absorbent articles, such as underwear, diapers, and washable or reusable absorbent articles such as woven training pants, absorbent swim pants, plastic training pants, and the like. Further, although discussed primarily in the context of toilet training for children, it should be understood that the present invention is applicable to adult personal care products such as absorbent incontinence undergarments and the like. The wetness indicator 39 may either be built directly into the article during manufacture or may be formed independently and attached to any of the aforementioned articles by the consumer. If the wetness indicator 39 is built directly into the article during manufacture, the wetness indicator may be optionally releasably attached so the consumer can remove the wetness indicator if desired.

Figure 2:
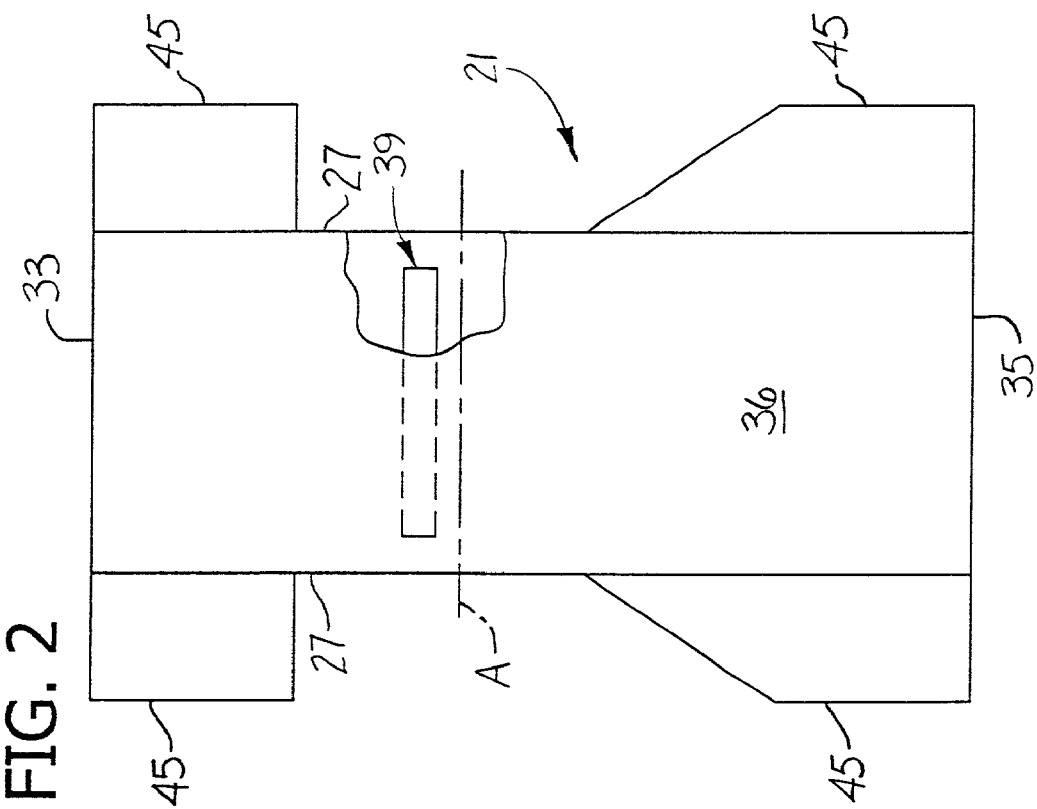
FIG. 2 is a schematic top plan of unfolded training pants of a first embodiment.

As illustrated in FIG. 2, a first embodiment of the wetness indicator 39 of the present invention is sized and shaped for positioning between the leg openings 27 of the pants 21. The training pants in FIG. 2 are depicted partially disassembled and unfolded to a flat position. The lateral edges 45 of the pants 21 are disconnected, exposing the flattened inner surface 36 of the pants, or the portion of the pants facing the wearer when the garment is worn. The wetness indicator 39 is positioned relative the inner surface 36 for alerting the wearer when the pants become sufficiently wet with liquid. Typically, the wetness indicator 39 is placed between the inner surface 36 and outer surface 37 (FIG. 1) to be hidden within the pants 21, such that the pliable wetness indicator is substantially imperceptible to the wearer before urination. However, those skilled in the art will appreciate the wetness indicator 39 may be positioned anywhere in the article where it is likely to become wet and be perceived by a wearer.

In one embodiment, the wetness indicator 39 is generally elongate, and remains elongate upon absorption of a preselected amount of liquid, as will be discussed in greater detail below. Although other orientations are contemplated as being within the scope of the invention, the wetness indicator 39 of one embodiment is oriented generally laterally within the garment, such that the longest dimension of the wetness indicator lies substantially parallel to a lateral axis A of the garment which extends between the leg openings 27. The periphery of the wetness indicator 39 of this embodiment is also generally rectangular in cross-section before absorption of the preselected amount of liquid, and after absorption, the wetness indicator becomes generally rounded. It is also contemplated that the wetness indicator 39 of the present invention may be formed in a shape other than a rectangle, without departing from the scope of the present invention.

Figure 4:
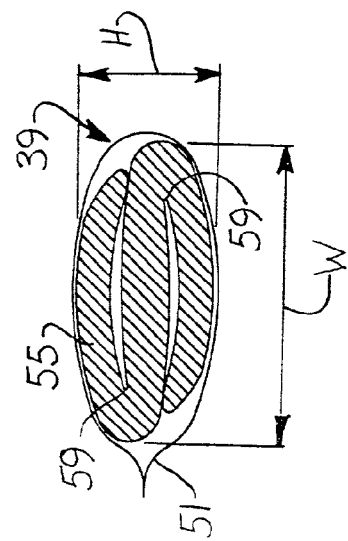
FIG. 4 is a schematic section of the wetness indicator taken in the plane of line 4-4 of FIG. 3.
Figure 3:
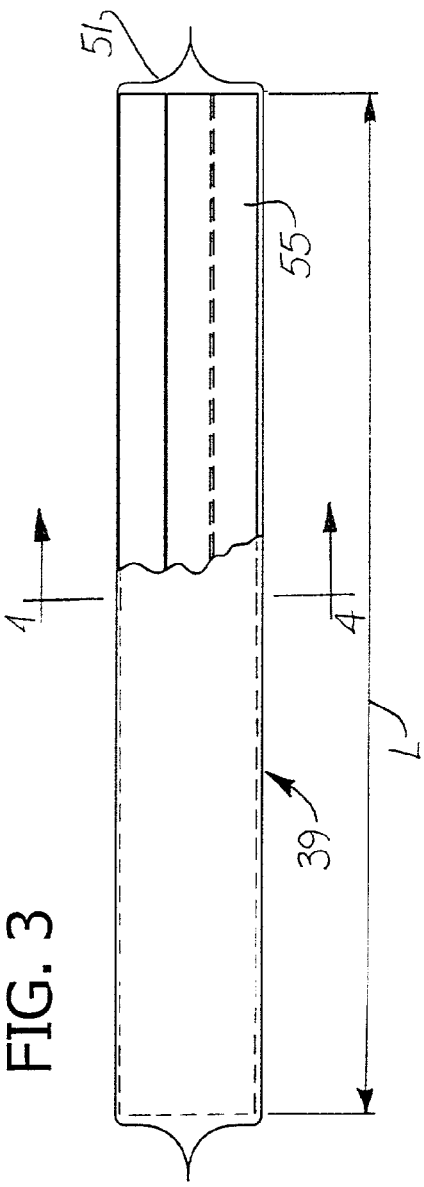
FIG. 3 is an enlarged schematic front elevation of a wetness indicator of the present invention partially broken away to show interior details.

Turning to the specific features of the wetness indicator 39, FIGS. 3 and 4 illustrate one embodiment. The wetness indicator 39 comprises a liquid permeable enclosure 51 having a liquid absorbent body 55 therein. Generally, such a body 55 comprises a thin sheet material laid over itself at least once to form at least two folds. In one embodiment, the absorbent body 55 is formed from thin sheet material fan folded longitudinally multiple times (e.g., two times) along multiple longitudinal fold lines 59 (FIG. 4) to form a multifold structure. Such a fan folded structure enhances the strength of the absorbent body 55 because each fold of material will act to support adjacent folds, further magnifying the expansive pressure within the enclosure 51. As such, the overall strength and stiffness of the absorbent body 55 increases in the direction of the fold line. The absorbent body 55 may have at least one longitudinal fold line, thereby forming at least two folds of absorbent sheet material. By varying the number of fold lines and the width of the folds, differently sized and shaped absorbent bodies 55 are possible. In one embodiment, the outer cross-section of the wetness indicator is generally rectangular when dry, expanding to a roughly oval shape after absorption, and having a width W less than four times its height H upon absorption of the preselected amount of liquid. For example, a square portion of material 6.4 centimeters (cm) per side and 0.065 cm thick is folded approximately in thirds to provide an absorbent body 55 having a width W of about 2.1 cm, a height H of about 0.195 cm and a length L of about 6.4 cm. The body 55 may be otherwise formed to facilitate expansion upon absorption of a preselected amount of liquid such as by being for placement within the enclosure 51. Other materials requiring no folds are also contemplated as within the scope of the present invention.

It is desirable that the absorbent body 55 be formed from a high absorbency under load (AUL) material. Although the absorbent body 55 may be made from other materials without departing from the scope of the present invention, in one embodiment the body is an Ultra Thin Absorbent (UTA) material comprising about fifty percent superabsorbent material and about fifty percent wood pulp and having a weight of about 225 grams per square meter (gsm) at a thickness of about 0.65 millimeter. One such UTA material can be produced using an online process such as described in U.S. application Ser. No. 09/939,061, entitled "Thin, High Capacity Absorbent Structure and Method for Producing Same," filed Aug. 24, 2001, by Sawyer, et al., which claims priority from U.S. Provisional Application No. 60/256,016, filed Dec. 20, 2000, both of which are hereby incorporated by reference. In addition, U.S. Pat. Nos. 5,147,343 (Kellenberger) and 5,601,542 (Melius et al.) describe other processes for producing UTA material. An alternate material is available from EAM Corporation of Jessup, Ga., under the trademark NovaThin® material. Although other materials may be used to form the enclosure 51 without departing from the scope of the present invention, in one embodiment the liquid permeable enclosure is formed from 20 gsm spunbond nonwoven available from Kimberly-Clark Corporation, Neenah, Wis. Such material may also be surface treated with about 0.45 weight percent of a surfactant mixture, such as AHCOVEL® N-62 chemical, available from Uniqema Inc., a division of ICI of New Castle, Del., or such as a surface treatment with an active ratio of about 3:1 of GLUCOPON® 220UP chemical, available from Cognis Corp. of Ambler, Pa. The surfactant may be applied to the entire surface of the spunbond nonwoven material, or it may be selectively applied to particular surface portions, such as to a surface portion facing the body.

It is contemplated that the enclosure 51 could also include liquid impermeable portions, such as those portions positioned away from the wearer without departing from the scope of the present invention.

When liquid flows through the liquid permeable enclosure 51 of the wetness indicator 39 and contacts the absorbent body 55, the liquid is absorbed by the body. Capillary, osmotic and absorptive forces draw the liquid into the wetness indicator 39. This absorption process helps draw liquid away from the skin of the wearer. As the wetness indicator 39 absorbs the liquid, the absorbent body 55 within the enclosure 51 begins swelling. When dry, the wetness indicator 39 is generally soft, pliable and cloth-like with a first stiffness similar to the other portions of the pants 21, making the presence of the wetness indicator 39 generally imperceptible to the wearer. The pliable wetness indicator 39 allows the thighs to move freely and easily compress the wetness indicator 39.

Once liquid is present in the pants 21 and the absorbent body 55 begins absorbing liquid, the absorbent body swells within the enclosure 51. Upon absorption of a preselected amount of liquid, the absorbent body 55 applies hydraulic pressure against the interior of the enclosure 51. Because the unrestrained saturated volume of the absorbent body 55 is greater than the volume of the enclosure 57, the liquid permeable enclosure limits expansion of the absorbent body, thereby stiffening the wetness indicator 39. As more liquid is absorbed by the body 55, the wetness indicator 39 becomes stiffer. Once the wetness indicator 39 absorbs the preselected amount of liquid, the wetness indicator reaches a second stiffness greater than the first stiffness. Such a stiffness provides a resistance to bending that may be readily perceived by the wearer.

Although the wetness indicator 39 may have other stiffnesses without departing from the scope of the present invention, in one configuration, tested previously and described below, the wetness indicator has a second stiffness about eleven times greater, on average, than its first stiffness. In another configuration, tested previously and described below, the second stiffness is about fourteen times greater, on average, than its first stiffness. The method for obtaining these stiffness measurements is described in the experiments detailed below. An effective wetness indicator 39 should have a second stiffness at least about five times greater than its first stiffness.

For example, a wetness indicator 39 with an average dry length of about 11.5 cm, an average dry width of about 2.0 cm and an average dry thickness of about 0.5 cm and composed of the materials described herein was used. Although the second stiffness may be measured upon absorption of a different amount of liquid without departing from the scope of the present invention, in one embodiment the second stiffness is measured upon absorption of about 33 grams of urine. However, those skilled in the art will appreciate that the amount of urine absorbed by the body 55 in actual use varies depending upon the size of the wetness indicator 39 and the materials used. In other words, the stiffness may be different in actual use.

The enclosure 51 of FIGS. 3 and 4 limits expansion of the absorbent body 55 in order for the enclosure to reach the second stiffness. If the liquid permeable enclosure 51 were too expandable, absorption of the preselected amount of liquid would simply expand the wetness indicator 39 without causing it to lose some of its pliability. In use, the pants 21 can be designed with the wetness indicator 39 positioned for resisting movement against the inner thighs of the wearer. Such resistive force exerted by the wetness indicator 39 upon the inner thighs is not large, but rather gently resists leg movement on the inside of the legs of the wearer such that the wearer perceives a resistive pressure, which he may learn to associate with urination. To further enhance the signaling properties of the wetness indicator 39, the liquid permeable enclosure 51 can be tightly wrapped about the liquid absorbent body 55. Wrapping the enclosure 51 tightly about the absorbent body 55, lowers the expandability of the absorbent body and decreases the amount of liquid required for the wetness indicator 39 to reach its second stiffness. The absorbent body 55 must not be wrapped too tightly, however, or the first stiffness of the wetness indicator 39 before absorbing liquid will be too great.

Furthermore, it is important that the preselected amount of liquid remain within the enclosure 51 even under outside pressure, such as applied by the leg of the wearer. If wearer movement forces liquid from the absorbent body 55 and out of the enclosure 51, the ability of the wearer to perceive a stiffened wetness indicator 39 decreases. Because the wearer may be active at the time of urination, the ability of the wetness indicator 39 to resist outside forces is key. If the amount of liquid in the enclosure 51 remains above the preselected amount, the hydraulic pressure within the enclosure, and therefore the stiffness of the wetness indicator 39, may be maintained continually for a sustained and perceptible indication that urination has occurred. Forming the absorbent body from an AUL material that resists releasing liquid, even under pressure.

Figure 5:
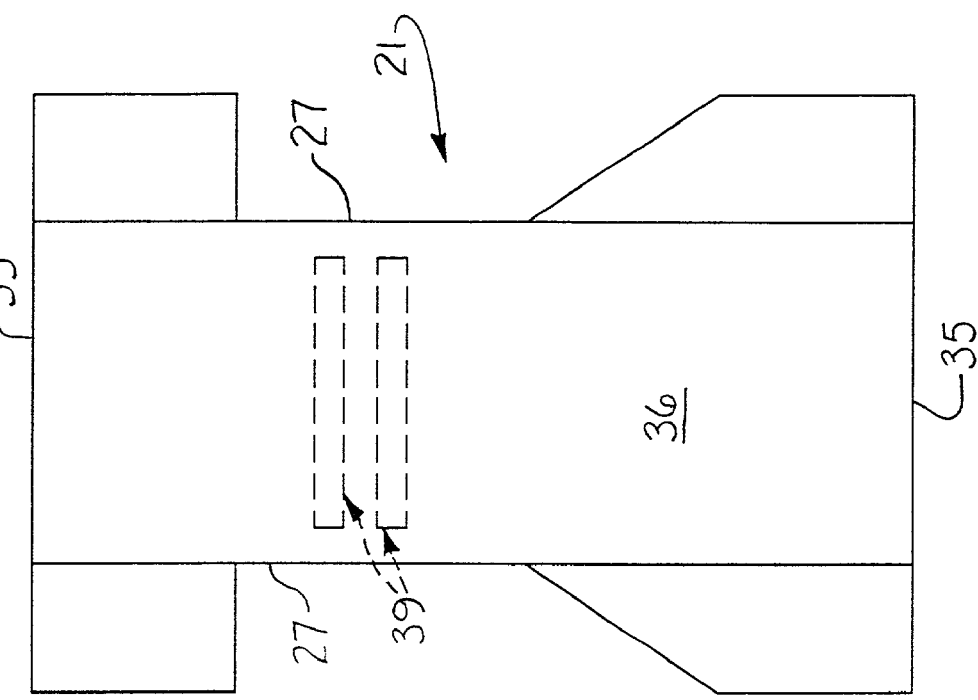
FIG. 5 is a schematic top plan of unfolded training pants of a second embodiment.

FIG. 5 depicts a second embodiment of the training pants 21 of the present invention in which two elongate wetness indicators 39 extend parallel to one another within the training pants 21. Although one wetness indicator 39 may sufficiently signal the wearer when urination has occurred, it is envisioned additional wetness indicators may further enhance the signal to the wearer. These wetness indicators 39 may be necessary for larger or older children with larger legs, who may find the resistive force provided by a single wetness indicator provides insufficient resistive force for perception. Further, the presence of two wetness indicators 39 permits one wetness indicator to be positioned where it is more likely to become wet upon urination by boys and one wetness indicator to be positioned where it is more likely to become wet upon urination by girls, thereby compensating for differences between the wetting patterns of boys and girls.

Figure 6:
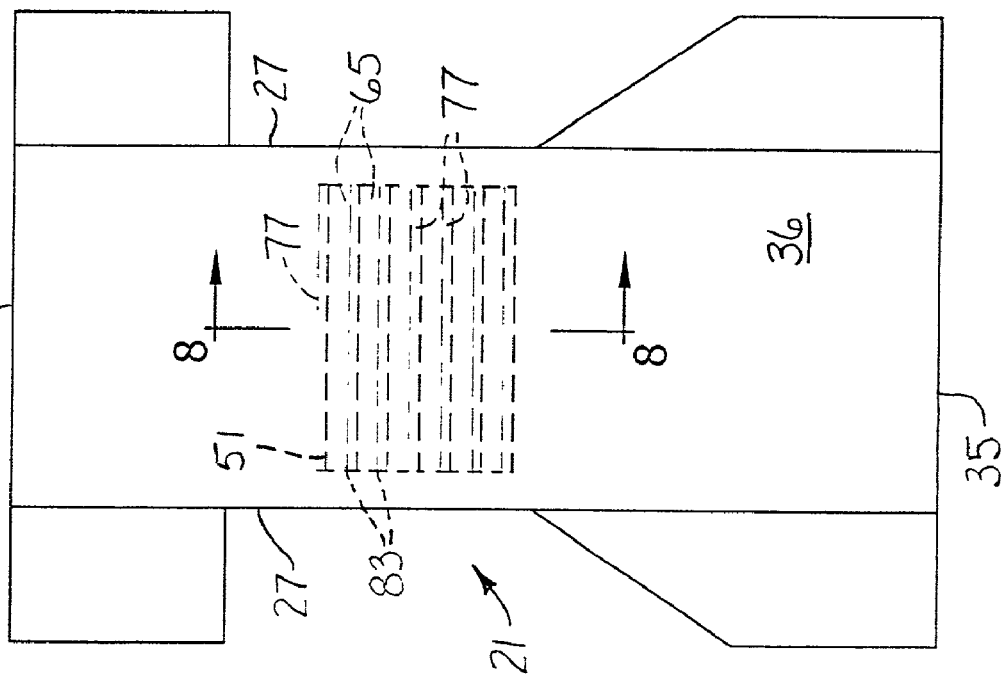
FIG. 6 is a schematic top plan of unfolded training pants of a third embodiment.

FIG. 6 illustrates a third embodiment of the present invention. The third embodiment of the training pants 21 includes a wetness indicator 39 having a large width W compared to its length L. For instance, the wetness indicator 39 in one embodiment has a width W between about one-fourth its length L and about three-fourths its length upon absorption of the preselected amount of liquid. Because the wetness indicator 39 has a large width W, it may be capable of absorbing more liquid than the wetness indicators of the first and second embodiments described above. Thus, it is envisioned that the wetness indicator 39 may be the only absorbent wetness indicator used in the training pants 21 of the third embodiment. Because such a wetness indicator 39 is capable of absorbing more liquid, it may provide a larger resistive pressure to the wearer due to its size.

Figure 7:
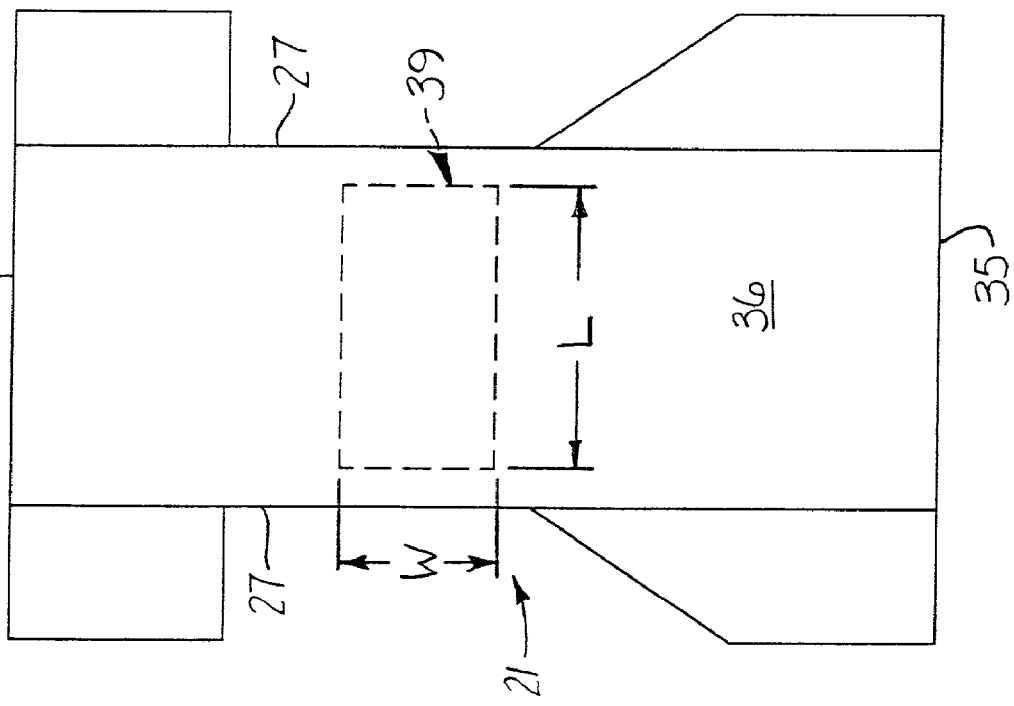
FIG. 7 is a schematic top plan of unfolded training pants of a fourth embodiment.
Figure 8:
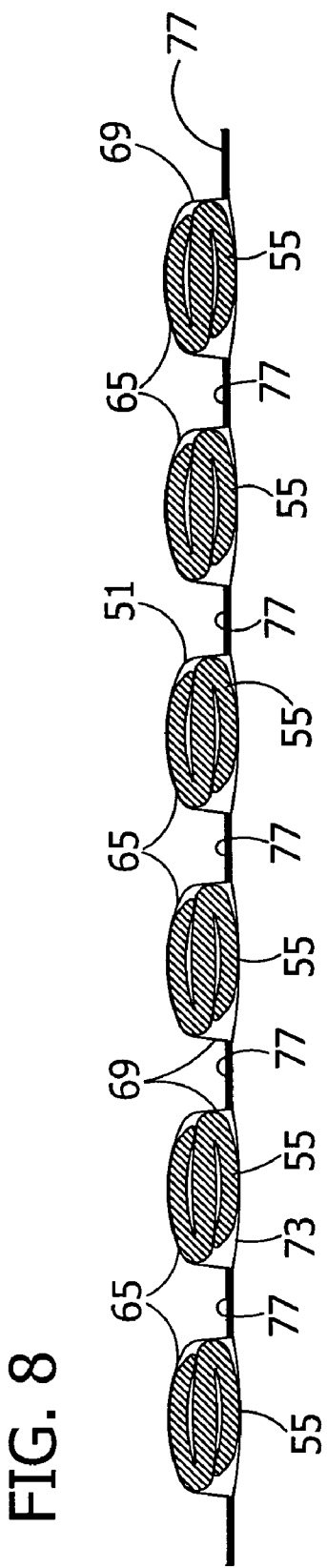
FIG. 8 is an enlarged schematic section of the training pants of the fourth embodiment taken in the plane of line 8-8 of FIG. 7.

FIGS. 7 and 8 depict a fourth embodiment of the present invention. Here, the training pants 21 include a liquid permeable enclosure 51 that has at least two chambers 65. Each chamber 65 contains a separate absorbent body 55 for absorbing liquid. In addition, each of the chambers 65 acts independently from the other chambers. In one embodiment, the chambers 65 are similarly sized and shaped, although differently sized and shaped chambers are also contemplated as being within the scope of the present invention. For instance, in the preferred embodiment, the chambers 65 are generally elongate and are oriented substantially parallel to each other. Such parallel chambers 65 act in concert by resisting flexure together against the legs of the wearer.

The chambers 65 are formed within the training pants 21 in a novel way. The enclosure 51 comprises a liquid permeable lining 69, which forms the inner surface 36 of the pants 21, and a base layer 73 bonded to one another along a series of parallel, spaced-apart seams 77, forming the chambers 65. These seams 77 may be formed by sonic bonding, with an adhesive or using any other conventional sealing process capable of forming seams between the lining 69 and the base layer 73. End portions 83 of the chambers 65 are also sealed (FIG. 7). Wetness indicators 39 having fewer or more chambers 65 are contemplated as being within the scope of the present invention, and the number and orientation of the chambers shown in FIGS. 7 and 8 are exemplary only.

As will be appreciated by those skilled in the art, the enclosure 51 described above may be an osmotic membrane and the absorbent body 55 may be a solution, a mixture, or a gel without departing from the scope of the present invention.

EXPERIMENT 1

An experiment was conducted to determine the change in stiffness of the wetness indicator from its first stiffness when dry to its second stiffness upon absorption of the preselected amount of liquid. The experiment entailed the use of ten sample wetness indicators having an average dry length of about 11.5 cm, an average dry width of about 2.0 cm and an average dry thickness of about 0.5 cm (not including the sonic seal about the edge as described below). The samples exhibited an average dry weight of about 2.6 grams. The samples were each formed as a liquid permeable enclosure having a liquid absorbent body therein. The liquid permeable enclosure comprised 20 gsm spunbond polyethylene available from Kimberly-Clark Corporation of Neenah, Wis. The spunbond polyethylene was surface treated with about a 0.45 weight percent surfactant mixture containing AHCOVEL® N-62 chemical and about a 3:1 active ratio of GLUCOPON® 220UP chemical. The liquid absorbent body comprised about ten percent Kraton® G2740X polymer, available from Kraton Polymers U.S. LLC of Houston, Tex., sixty percent Favor® SXM 880 Super Absorbent Material from Stockhausen, Inc. of Greensboro, N.C., and thirty percent Sulfatate-HJ-FA Kraft, Southern Hardwood Pulp from Rayonier, Inc. of Jacksonville, Fla. The liquid absorbent body was generally formed as a sheet-like material 5 cm wide and 11 cm long, fan folded lengthwise into thirds and placed inside the liquid permeable enclosure. To help the absorbent body hold its shape, an adhesive transfer tape (Model No. 922XL, 1.3 cm wide, 0.05 millimeter thick adhesive transfer tape from 3M, Inc. of St. Paul, Minn.) was placed between the outermost layer of the absorbent body and the remainder of the absorbent body, to retain the body in its folded configuration. In addition, the material of the liquid permeable enclosure was sonically bonded to itself for about 0.1 seconds at a pressure of 150 kiloPascals on a Branson 920 Sonic Bonder, available from Branson Ultrasonics, Inc. of Danbury, Conn., forming an enclosure for the absorbent body.

For each of the ten samples tested, the sample was placed across a pair of upright supports spaced 5 cm apart with about 4 cm of each end of the wetness indicator extending over each support. The supports were placed upon a tared scale so that additional vertical loads could be recorded. A testing probe having a width greater than the width of the wetness indicator and a thickness of 0.2 cm was then pressed downward upon the wetness indicator midway between the supports, thereby bending the wetness indicator and deflecting the center of the wetness indicator downward. The probe deflected the wetness indicator about 1.2 cm down from the initial horizontal position and a reading was recorded from the scale. An increase in such a reading beyond the weight of the supports and the wetness indicator indicated the force required to bend the wetness indicator, or the relative stiffness of the wetness indicator.

Once the ten samples were deflected in their dry condition, the samples were each tested again after soaking for five minutes in a 0.9% by volume Aqueous Solution Isotonic Saline (i.e., Sodium Chloride) available from Ricca Chemical Company of Arlington, Tex. The saline solution served as an approximation of urine. The five minute soak time ensured adequate saturation of the sample. After absorption, each sample was drained for one minute on a paper towel. In the saturated condition, the length and width dimensions of the wetness indicator remained unchanged, about 11.5 cm by about 2.9 cm, respectively, while the thickness of the wetness indicator increased to about 2.0 cm. In addition, the cross-sectional shape of the wetness indicator changed from a flattened rectangle to a generally rounded shape. The sample was then placed upon the supports for the same 1.2 cm deflection noted above, again recording the load on the scale during the deflection.

On average, the load recorded for the ten dry samples during deflection was 36 grams. Subtracting the average weight of the wetness indicators themselves, 2.6 grams, this portion of the experiment indicated that a load of about 33 grams was required to deflect the wetness indicator about 1.2 cm downward from the initial horizontal position. In contrast, the load recorded for the same ten samples after absorption indicated an average load during deflection of 405 grams. Subtracting the average weight of the wetness indicators after absorption, 25 grams, the deflection load for the wetness indicator was 380 grams, on average. Thus, after absorption of liquid, the wetness indicator described above is over eleven times stiffer in bending than in its dry condition (380/33=11.5). As used herein, "stiffness" means the force exerted upon the wetness indicator divided by the deflection. Here, where the deflection of each test was identical, the definition of stiffness is directly related to the recorded force. This experiment validated the assertion that the stiffness of the wetness indicator increased after absorption of liquid.

EXPERIMENT 2

An experiment was conducted to determine the change in stiffness of another wetness indicator from its first stiffness when dry to its second stiffness upon absorption of the preselected amount of liquid. The deflection experiment was essentially the same as noted above, except that the wetness indicator itself was formed differently. Here, the liquid absorbent body was formed from a sheetlike material 3.8 cm wide and 11 cm long, folded lengthwise into half and positioned inside the liquid permeable enclosure. The overall size of the wetness indicator was 11.5 cm long, 2.0 cm wide and 0.3 cm thick (not including the sonic seal around the edge). In the saturated condition, the length dimension of the wetness indicator remained unchanged, about 11.5 cm, while the thickness of the wetness indicator increased to about 1.5 cm and the width decreases to about 1.5 cm. In addition, the cross-sectional shape of the wetness indicator changed from a flattened rectangle to a more rounded shape, as with the wetness indicator of the first experiment.

On average, the load recorded for the ten dry samples during the 1.2 cm downward deflection from the initial horizontal position was 16 grams. Subtracting the average weight of the wetness indicators themselves, 2.2 grams, this experiment indicated a load of about 14 grams was required to deflect the wetness indicator in a dry condition about 1.2 cm. In contrast, the load recorded for the same ten samples after absorption indicated an average load during deflection of 223 grams. Subtracting the average weight of the wetness indicators after absorption, 22 grams, the deflection load for the wetness indicator was 201 grams, on average. Thus, after absorption of liquid, the wetness indicator described above was over fourteen times stiffer in bending than in its dry condition (201/14=14.4). Therefore, a wetness indicator should provide a second stiffness that is at least about five times greater than its first stiffness. More particularly, the second stiffness is between about five and about twenty-five times greater than the first stiffness. Preferably the second stiffness is between about ten and about fifteen times greater than the first stiffness.

Comparing the results of experiments 1 and 2, one skilled in the art would readily understand how to create a wetness indicator of varying stiffness by altering the size, materials and shape of the experimental wetness indicators. The wetness indicators disclosed in experiments 1 and 2 are included for demonstrative purposes only and should not be construed to limit the scope of the present invention. For example, wetness indicators could easily be made longer, shorter, thicker, thinner, wider, narrower or in a different configuration altogether without departing from the scope of the present invention.

When introducing elements of the present invention or the preferred embodiment(s) thereof, the articles "a", "an", "the", and "said" are intended to mean that there are one or more of the elements. The terms "comprising," "including", and "having" are intended to be inclusive and mean that there may be additional elements other than the listed elements.

As various changes could be made in the above constructions without departing from the scope of the invention, it is intended that all matter contained in the above description or shown in the accompanying drawings shall be interpreted as illustrative and not in a limiting sense.

What is claimed is:

1. A wetness indicator for alerting a wearer to urination comprising a liquid permeable enclosure having an interior volume and a liquid absorbent body therein, said liquid absorbent body absorbing liquid in the presence thereof and having an unrestrained volume upon absorption of a preselected amount of liquid, said unrestrained volume of the absorbent body being substantially greater than the interior volume of the enclosure such that the absorbent body applies an expansion pressure to the enclosure upon absorption of said preselected amount of liquid, said enclosure limiting expansion of the absorbent body so that the wetness indicator stiffens as liquid is absorbed, said wetness indicator having a first stiffness when dry and a second stiffness greater than said first stiffness upon absorption of said preselected amount of liquid.

2. A wetness indicator as set forth in claim 1 wherein said wetness indicator is generally elongate.

3. A wetness indicator as set forth in claim 1 wherein said absorbent body comprises a sheet laid over itself at least once to form at least two folds.

4. A wetness indicator as set forth in claim 3 wherein said absorbent body is formed from thin sheet material fan folded longitudinally multiple times to form a multifold structure.

5. A wetness indicator as set forth in claim 2 wherein said wetness indicator is generally rounded upon absorption of said preselected amount of liquid.

6. A wetness indicator as set forth in claim 5 wherein said wetness indicator has a width between about one-fourth its length and about three-fourths its length.

7. A wetness indicator as set forth in claim 1 wherein said enclosure has at least two chambers.

8. A wetness indicator as set forth in claim 7 wherein said chambers are generally elongate and parallel.

9. A wetness indicator as set forth in claim 7 wherein said enclosure comprises a liquid permeable lining and a base layer attached to said lining to form said chambers between the base layer and the lining.

10. A wetness indicator as set forth in claim 9 wherein said base layer is bonded to said lining along a series of parallel, spaced-apart seams.

11. A wetness indicator as set forth in claim 1 in combination with a garment, said wetness indicator being positioned in a crotch region of the garment.

12. A garment comprising an inner surface facing a wearer when wearing the garment, and a wetness indicator positioned relative to the inner surface for alerting the wearer when the inner surface becomes wet with liquid, said wetness indicator having a first stiffness when dry and a second stiffness greater than said first stiffness upon absorption of a preselected amount of liquid, said wetness indicator comprising a liquid permeable enclosure having an interior volume and a liquid absorbent body therein, the absorbent body having an unrestrained saturated volume greater than the interior volume of the liquid permeable enclosure.

13. A garment as set forth in claim 12 wherein said wetness indicator is positioned in the garment to press on the inner thighs of the wearer.

14. A garment as set forth in claim 12 wherein said garment comprises toilet training pants.

15. A garment as set forth in claim 12 wherein said wetness indicator is generally elongate.

16. A garment as set forth in claim 12 wherein said second stiffness is at least about five times greater than said first stiffness.

17. A garment as set forth in claim 16 wherein said second stiffness is between about five and about twenty-five times greater than said first stiffness.

18. A garment as set forth in claim 17 wherein said second stiffness is between about ten and about fifteen times greater than said first stiffness.

19. A garment as set forth in claim 12 wherein said enclosure has at least two generally elongate and parallel chambers.

20. A garment as set forth in claim 12 wherein said second stiffness is at least about five times greater than said first stiffness.

21. A garment as set forth in claim 20 wherein said second stiffness is between about five and about twenty-five times greater than said first stiffness.

22. A garment as set forth in claim 21 wherein said second stiffness is between about ten and about fifteen times greater than said first stiffness.

23. An article for personal wear capable of alerting a wearer to the wearer's release of liquid body exudates, the article comprising a front region, a back region and a crotch region interconnecting the front and back regions and extending generally longitudinally therebetween, and a generally elongate wetness indicator positioned in said crotch region so as to come in contact with the liquid body exudates, said wetness indicator having a first stiffness when dry and a second stiffness greater than said first stiffness upon absorption of a preselected amount of the liquid body exudates, said wetness indicator being positioned transversely in the crotch region such that opposite ends of said wetness indicator provide a tactile sensation to the inner thighs of the wearer for alerting the wearer to the release of liquid body exudates.

24. An article as set forth in claim 23 wherein the wetness indicator comprises a liquid permeable enclosure and an absorbent body within said liquid permeable enclosure, said absorbent body being capable of expansion upon the absorption of liquid body exudates thereby, said enclosure limiting the expansion of the absorbent body whereby the wetness indicator stiffens as liquid body exudates are absorbed by said absorbent body.

25. An article as set forth in claim 24 wherein said second stiffness is at least about five times greater than said first stiffness.

26. An article as set forth in claim 24 wherein an unrestrained saturated volume of the liquid absorbent body is greater than the volume of the liquid permeable enclosure.

27. A wetness indicator as set forth in claim 1 wherein said second stiffness is at least about five times greater than said first stiffness.

28. A garment as set forth in claim 13 wherein said wetness indicator is generally elongate and is transversely positioned in a crotch region of the garment such that opposite ends of the elongate wetness indicator provide a tactile sensation to the inner thighs of the wearer.

* * * * *